United States Patent [19]
Jonassen et al.

[11] Patent Number: 5,869,602
[45] Date of Patent: *Feb. 9, 1999

[54] PEPTIDE DERIVATIVES

[75] Inventors: Ib Jonassen, Valby; Svend Havelund, Bagsvaerd; Per Hertz Hansen, Lyngby; Peter Kurtzhals, Taastrup; John Halstrøm, Hundested, all of Denmark

[73] Assignee: Novo Nordisk A/S, Bagsvaerd, Denmark

[ * ] Notice: This patent issued on a continued prosecution application filed under 37 CFR 1.53(d), and is subject to the twenty year patent term provisions of 35 U.S.C. 154(a)(2).

[21] Appl. No.: 448,219

[22] Filed: May 23, 1995

[30] Foreign Application Priority Data

Mar. 17, 1995 [DK] Denmark .................. 0275/95

[51] Int. Cl.$^6$ .................................................. C07K 7/00
[52] U.S. Cl. ............................................ 530/308; 530/300
[58] Field of Search .................................. 530/300, 308; 514/8, 26, 23

[56] References Cited

U.S. PATENT DOCUMENTS

| | | | |
|---|---|---|---|
| 4,430,326 | 2/1984 | Hruby et al. ........................... | 424/177 |
| 5,135,736 | 8/1992 | Anderson et al. ..................... | 424/1.1 |
| 5,359,030 | 10/1994 | Ekwuribe .............................. | 530/303 |

FOREIGN PATENT DOCUMENTS

| | | |
|---|---|---|
| 0 511 600 | 11/1992 | European Pat. Off. . |
| WO 93/15750 | 8/1993 | WIPO . |
| WO 93/21320 | 10/1993 | WIPO . |

OTHER PUBLICATIONS

Tenma et al. Pharmaceutical Research. vol. 10. No. 10. Development of New Lipophilic Derivatives of Tetragastrin: Physiochemical Characteristics and Intestinal Absorption of Acyl–tetragastrin Derivatives in Rats. pp. 1488–1492, Oct. 1993.

Muranishi S. et al., Abstract, J. Control, vol. 19, pp. 179–188, Dialog Accn. No. 8421240 (1992).

Tenma T. et al., Abstract, Pharmaceutical Research, vol. 10, No. 10, pp. 1488–1492, Dialog Assn. No. 12616071 (1993).

Yodoya et al., Abstract, J. Pharmacology, vol. 271, No. 3, pp. 1509–1513, Dialog Assn. No. 13565514 (1994).

Cruz, M.E.M. et al., Chem. Abs., Proc. Int. Symp. Contr. Rel. Bioact. Mater., vol. 123, No. 10, pp. 345–347 (1995).

Martins, M.B. et al., Chem. Abs., Proc. Int. Symp. Contr. Rel. Bioact. Mater., vol. 118, No. 16, pp. 524–525 (1993).

*Primary Examiner*—Cecilia J. Tsang
*Assistant Examiner*—C. Delacroix-Muirheid
*Attorney, Agent, or Firm*—Steve T. Zelson, Esq.; Valeta Gregg, Esq.

[57] ABSTRACT

The present invention relates to a pharmacologically active peptide hormone derivative in which the parent peptide hormone has been modified by introducing either a lipophilic substituent, W, in the N-terminal amino acid or a lipophilic substituent, Z, in the C-terminal amino acid of the parent peptide hormone or an analogue thereof, said lipophilic substituent having from 8 to 40 carbon atoms, has a protracted profile of action.

3 Claims, No Drawings

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

Ala   Pro   Gly   Pro   Arg   Lys
                                  5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

Xaa  Leu  Phe  Xaa  Tyr  Lys
                      5

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

Tyr  Ala  Gly  Phe  Leu  Lys
                      5

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

Pro  His  Pro  Phe  His  Phe  Phe  Val  Tyr
                      5

( 2 ) INFORMATION FOR SEQ ID NO:5:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

Ser  Leu  Arg  Arg  Ser  Ser  Cys  Phe  Gly  Gly  Arg  Met  Asp  Arg  Ile  Gly
                      5                          10                           15

Ala  Gln  Ser  Gly  Leu  Gly  Cys  Asn  Ser  Phe  Arg  Tyr  Lys
               20                          25

PEPTIDE DERIVATIVES

FIELD OF THE INVENTION

The present invention relates to novel derivatives of peptide hormones and analogues thereof which have a protracted profile of action and to methods of making and using them.

BACKGROUND OF THE INVENTION

Peptide hormones are widely used in medical practice and since they can be produced by recombinant DNA technology it can be expected that their importance will increase also in the years to come. When native peptide hormones or analogues thereof are used in therapy it is generally found that they have a high clearance rate. A high clearance rate of a therapeutic agent is inconvenient in cases where it is desired to maintain a high blood level thereof over a prolonged period of time since repeated administrations will then be necessary. Examples of peptide hormones which have a high clearance rate are: ACTH, corticotropin-releasing factor, angiotensin, calcitonin, insulin and fragments and analogues thereof, glucagon, glucagon-like peptide and analogues and fragments thereof, IGF-1, IGF-2, enterogastrin, somatostatin, somatotropin, somatomedin, parathyroid hormone, thrombopoietin, erythropoietin, hypothalamic releasing factors, prolactin, thyroid stimulating hormones, endorphins, enkephalins, vasopressin, oxytocin, opiods and analogues thereof, superoxide dismutase, interferon, asparaginase, arginase, arginine deaminase, adenosine deaminase and ribonuclease.

Although it has in some cases been possible to influence the release profile of peptide hormones by applying suitable pharmaceutical compositions this approach has various shortcomings and is not generally applicable. Accordingly, there still is a need for improvements in the field of administration of peptide hormones.

SUMMARY OF THE INVENTION

In the present text, the term peptide is used to designate both small peptides and polypeptides and proteins. The terms peptide and peptide hormone are used as encompassing both naturally occurring and synthetic peptide hormones and fragments and analogues thereof. Analogues are peptides in which one or more amino acids in the parent peptide have been deleted or substituted by another amino acid, or to which one or more amino acids have been added, and which still have qualitatively—but not necessarily quantitatively—the same pharmacological effect as the parent peptide.

The present invention relates generally to novel derivatives of peptide hormones which have a protracted profile of action.

Thus, in its broadest aspect, the present invention relates to a pharmacologically active peptide hormone which has been modified by introducing a lipophilic substituent comprising from 8 to 40 carbon atoms in either the N-terminal or the C-terminal amino acid of the native peptide hormone or an analogue thereof, with the proviso that when the lipophilic substituent is attached to the N-terminal amino group then the substituent comprises a group which can be negatively charged and with the further proviso, that said peptide hormone is not insulin or an analogue thereof.

In one preferred embodiment of the present invention, a carboxyl group contained in the lipophilic group, W, forms an amide bond together with the α-amino group of the N-terminal amino acid.

In another preferred embodiment of the present invention, a carboxyl group contained in the lipophilic group, W, forms an amide bond together with the ε-amino group of a N-terminal lysine.

In another preferred embodiment of the present invention, the lipophilic group, W, is composed of a spacer and a bulk lipophilic substituent. The spacer is preferably succinic acid, Glu or Asp. The bulk lipophilic substituent is preferably a straight chain fatty acid which optionally has an amino group. When succinic acid is used as spacer, one of its carboxyl groups forms an amide bond with an amino group in the N-terminal amino acid while the other carboxyl group forms an amide bond with an amino group contained in the bulk lipophilic group. When Glu or Asp is used as spacer, one of the carboxyl groups forms an amide bond with an amino group in the N-terminal amino acid while the bulk lipophilic substituent preferably is the acyl group of a straight chain fatty acid or of an acid which comprises a partly or completely hydrogenated cyclopentanophenanthrene skeleton which acyl group is attached to the amino group of the spacer.

In another preferred embodiment of the present invention, an amino group contained in the lipophilic group Z forms an amide bond together with carboxyl group of the C-terminal amino acid of the parent peptide.

In another preferred embodiment of the present invention, Z is a straight chain fatty acid which has an amino group.

In another preferred embodiment of the present invention, Z has a group which can be negatively charged.

In another preferred embodiment of the present invention, Z has a free carboxylic acid group.

In another preferred embodiment of the present invention, the lipophilic group Z is composed of a spacer and a bulk lipophilic substituent. The spacer is preferably Lys, Glu or Asp. When Lys is used as spacer, the bulk lipophilic substituent, in one preferred embodiment, is the acyl group of a straight chain fatty acid or of an acid which comprises a partly or completely hydrogenated cyclopentanophenanthrene skeleton which acyl group is attached to the amino group of the spacer group. In a further preferred embodiment, when Lys is used as spacer, a further spacer is inserted between the ε-amino group of Lys and the bulk lipophilic substituent. In one preferred embodiment, such a further spacer is succinic acid which forms an amide bond with the ε-amino group of Lys and with an amino group present in the bulk lipophilic substituent. In another preferred embodiment such a further spacer is Glu or Asp which form one amide bond with the ε-amino group of Lys and a further amide bond with a carboxyl group present in the bulk lipophilic substituent which is preferably a straight chain fatty acid or an acid which comprises a partly or completely hydrogenated cyclopentanophenanthrene skeleton.

In another preferred embodiment, the present invention relates to the use of the peptide derivatives of the invention as medicaments.

In another preferred embodiment, the present invention relates to medicaments containing the peptide derivatives of the invention.

In another preferred embodiment, the present invention relates to the a pharmaceutical composition for the treatment of osteoporosis in a patient in need of such a treatment, comprising a therapeutically effective amount of an IGF-1 derivative according to the invention together with a pharmaceutically acceptable carrier.

In another preferred embodiment, the present invention relates to a method of treating osteoporosis in a patient in need of such a treatment comprising administering to the patient a therapeutically effective amount of an IGF-1 derivative according to the invention together with a pharmaceutically acceptable carrier.

Examples of parent peptide hormones which are of interest in connection with the present invention are the following: ACTH, corticotropin-releasing factor, angiotensin, calcitonin, glucagon, glucagon-like peptide and analogues and fragments thereof, IGF-1, IGF-2, enterogastrin, somatostatin, somatotropin, somatomedin, parathyroid hormone, thrombopoietin, erythropoietin, hypothalamic releasing factors, prolactin, thyroid stimulating hormones, endorphins, enkephalins, vasopressin, oxytocin, opiods and analogues thereof, superoxide dismutase, interferon, asparaginase, arginase, arginine deaminase, adenosine deaminase and ribonuclease.

Examples of particularly preferred derivatives of IGF-1 and IGF-1 analogues are:

$Lys^{69}(N^{\epsilon}$-tetradecanoyl) des(70) human IGF-1;

$Ser^{69}$-$NH(CH_2)_n COOH$ des(70) human IGF-1 wherein n is an integer from 12 to 24;

$Ser^{69}$-$NH(CH_2)_n CH_3$ des(70) human IGF-1 wherein n is an integer from 12 to 24;

$Lys^{71}(N^{\epsilon}$-tetradecanoyl) human IGF-1;

$Ala^{70}$-$NH(CH_2)_n COOH$ human IGF-1 wherein n is an integer from 12 to 24; and $Ala^{70}$-$NH(CH_2)_n CH_3$ human IGF-1 wherein n is an integer from 12 to 24.

A preferred derivative of enterogastrin is:

H-Ala-Pro-Gly-Pro-Arg-Lys($\epsilon$-tetradecanoyl)-OH. H-(SEQ ID NO:1)($N^{\epsilon}$-tetradecanoyl)-OH

DETAILED DESCRIPTION OF THE INVENTION

Pharmaceutical compositions

Pharmaceutical compositions containing a peptide derivative according to the present invention may be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. A further option is a composition which may be a powder or a liquid for the administration of the peptide derivative in the form of a nasal spray. As a still further option, it may also be possible to administer the peptide derivatives transdermally.

Pharmaceutical compositions containing a compound of the present invention may be prepared by conventional techniques, e.g. as described in *Remington's Pharmaceutical Sciences*, 1985.

Thus, the injectable compositions of the peptide derivatives of the invention can be prepared using the conventional techniques of the pharmaceutical industry which involves dissolving and mixing the ingredients as appropriate to give the desired end product.

Thus, according to one procedure, the peptide derivative is dissolved in an amount of water which is somewhat less than the final volume of the composition to be prepared. An isotonic agent, a preservative and a buffer is added as required and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

Examples of isotonic agents are sodium chloride, mannitol and glycerol.

Examples of preservatives are phenol, m-cresol, methyl p-hydroxybenzoate and benzyl alcohol.

Examples of suitable buffers are sodium acetate and sodium phosphate.

A composition for nasal administration of certain peptide hormones may, for example, be prepared as described in European Patent No. 272097 (to Novo Nordisk A/S).

The peptide derivatives of this invention can be used in the treatment of various diseases. The particular peptide derivative to be used and the optimal dose level for any patient will depend on the disease to be treated and on a variety of factors including the efficacy of the specific peptide derivative employed, the age, body weight, physical activity, and diet of the patient, on a possible combination with other drugs, and on the severity of the case. It is recommended that the dosage of the peptide derivative of this invention be determined for each individual patient by those skilled in the art in a similar way as for known peptide hormones.

The present invention is further illustrated by the following examples which, however, are not to be construed as limiting the scope of protection. The features disclosed in the foregoing description and in the following examples may, both separately and in any combination thereof, be material for realizing the invention in diverse forms thereof.

EXAMPLES

Abbreviations:

Fmoc: 9-fluorenylmethyloxycarbonyl.

For: formyl

Dde: 1-(4,4-dimethyl-2,6-dioxocyclohexylidine)-ethyl.

DMF: N,N-dimethylformamide.

Tbu: tert-butyl.

Acm: acetaindomethyl.

DIC: N,N-diisopropylcarbodiimide.

HOBT: 1-hydroxybenzotriazole.

TFA: trifluoroacetic acid.

Analytical

Molecular masses of the products prepared were obtained by plasma desorption mass spectrometry (PDMS) using Bio-Ion 20 instrument (Bio-Ion Nordic AB, Uppsala, Sweden).

Determination of lipophilicity.

The lipophilicity of peptides and peptide derivatives relative to human insulin, $k'_{rel}$, was measured on a LiChrosorb RP18 (5 $\mu$m, 4×250 mm) HPLC column by isocratic elution at 40° C. using mixtures of A) 0.1M sodium phosphate buffer, pH 7.3, containing 10% acetonitrile, and B) 50% acetonitrile in water as eluents. The elution was monitored by following the UV absorption of the eluate at 214 nm. Void time, $t_0$, was found by injecting 0.1 mM sodium nitrate. Retention time for human insulin, $t_{insulin}$, was adjusted to at least $2t_0$ by varying the ratio between the A and B solutions. $k'_{rel}=(t_{derivate}-t_0)/(t_{insulin}-t_0)$.

Example 1

Synthesis of For-Nle-Leu-Phe-Nle-Tyr-Lys($N^{\epsilon}$-tetradecanoyl)-OH For-(SEQ ID NO:2)($N^{\epsilon}$-tetradecanoyl)-OH.

For-Nle-Leu-Phe-Nle-Tyr-Lys-OH For-(SEQ ID NO:2)-OH, was purchased from Bachem Feinchemikalien AG, Switzerland. The peptide is a potent chemoattractant for human neutrophils. The title compound was prepared by dissolving 17 mg of For-Nle-Leu-Phe-Nle-Tyr-Lys-OH in 5 ml of DMF and then adding 35 $\mu$l of triethylamine followed by 20 mg of solid tetradecanoic acid succinimidyl-N-hydroxy ester to the solution. The reaction was monitored by RP-HPLC employing a column packed with reversed phase C18 silica material. For the elution was used a gradient from 30% ethanol to 80% ethanol in 0.1% aqueous TFA. The product was purified on a column (length 250 mm diameter 20 mm) packed with C18 silica reversed phase material. The compound was dissolved in 74% ethanol/0.1% aqueous TFA and subsequently applied to the column and purified at 40° C. by isocratic elution in the same buffer at a flow rate of 6 ml/hour. The yield was 20 mg. The identity of the compound was confirmed by PDMS.

Molecular mass, found by PDMS: 1034, theory: 1034.

The lipophilicity of the title compound relative to human insulin was found to be $8.2 \times 10^3$.

Reference

The reference compound, For-Nle-Leu-Phe-Nle-Tyr-Lys-OH, was purchased from Bachem Feinchemikalien AG, Switzerland, and used as received. The lipophilicity of the reference compound relative to human insulin was found to be 2.3.

Example 2

Synthesis of H-Tyr-D-Ala-Gly-Phe-Leu-Lys(N$^\epsilon$tetradecanoyl)-OH H-(SEQ ID NO:3)(N$^\epsilon$-tetradecanoyl)-OH.

The enkephalin derivative H-Tyr-D-Ala-Gly-Phe-Leu-Lys(N$^\epsilon$-tetradecanoyl)-OH H-(SEQ ID NO:3)(N$^\epsilon$-tetradecanoyl)-OH was made from Boc-Tyr-D-Ala-Gly-Phe-Leu-Lys-OH Boc-(SEQ ID NO:3)-OH (A-2435 Bachem Feinchemikalien AG, Switzerland). The Boc-Tyr-D-Ala-Gly-Phe-Leu-Lys-OH Boc-(SEQ ID NO:3)-OH was acylated using tetradecanoic acid succinimidyl-N-hydroxy ester as described in Example 1. The reaction mixture was evaporated to dryness and the residue was dissolved in TFA and evaporated to dryness, solubilized in ethanol/water/0.1% and purified by RP-HPLC as described in Example 1. The yield was 15 mg.

Molecular mass, found by PDMS: 909, theory: 907.

The lipophilicity of the title compound relative to human insulin was found to be $2.3 \times 10^3$.

Reference

The reference compound, H-Tyr-D-Ala-Gly-Phe-Leu-Lys-OH H-(SEQ ID NO:3)-H, was synthesized from Boc-Tyr-D-Ala-Gly-Phe-Leu-Lys-OH Boc-(SEQ ID NO:3)-OH by dissolving 20 mg of this compound in 200 µl of TFA and evaporating to dryness. The residue was dissolved in 5% acetic acid and freeze dried. The lipophilicity of the reference compound relative to human insulin was found to be $3.0 \times 10^{-3}$.

Example 3

Synthesis of H-Pro-His-Pro-Phe-His-Phe-Phe-Val-Tyr-Lys(N$^\epsilon$-tetradecanoyl)-OH H-(SEQ ID NO:4)(N$^\epsilon$-tetradecanoyl)-OH Fmoc-Pro-His-Pro-Phe-His-Phe-Phe-Val-Tyr-Lys-OH Fmoc-(SEQ ID NO:4)-OH (obtained from Bachem Feinchemikalien AG, Switzerland) which is a potent inhibitor of renin was allowed to react with tetradecanoic acid succinimidyl-N-hydroxy ester as described in Example 1. After the acylation reaction, the Fmoc group was removed by addition of piperidine to the reaction mixture to a final concentration of 20%. The title compound was isolated by RP-HPLC as described in Example 1. The yield was 23 mg.

Molecular mass, found by PDMS: 1529.6, theory: 1529.

The lipophilicity relative to human insulin was found to be $5.3 \times 10^3$.

Reference

The reference compound, H-Pro-His-Pro-Phe-His-Phe-Phe-Val-Tyr-Lys-OH, was synthesized from Fmoc-Pro-His-Pro-Phe-His-Phe-Phe-Val-Tyr-Lys-OH (obtained from Bachem Feinchemikalien AG, Switzerland). Thus, 20 mg of Fmoc-Pro-His-Pro-Phe-His-Phe-Phe-Val-Tyr-Lys-OH Fmoc-(SEQ ID NO:4)-OH was dissolved in 500 µl of 20% piperidine in DMF and left for 20 min. The reference compound was purified by RP-HPLC as described in Example 1.

The lipophilicity of the reference compound relative to human insulin was found to be $2.3 \times 10^2$.

Example 4

Synthesis of Arg$^4$,Arg$^9$,Lys$^{15}$(N$^\epsilon$-tetradecanoyl) somatostatin.

The title compound was synthesized from Fmoc-Arg$^4$, Arg$^9$,Lys$^{15}$ somatostatin which was obtained from Saxon Biochemicals GMBH, Hannover, Germany. 50 mg of Fmoc-Arg$^4$,Arg$^9$,Lys$^{15}$ somatostatin was dissolved in a mixture of 346 µl of DMF and 53.9 µl of 4-methylmorpholine. The mixture was cooled to 15° C. and 15.9 mg of tetradecanoic acid succinimidyl-N-hydroxy ester dissolved in 100 µl of DMF was added. The reaction was allowed to proceed for 3 hours and 20 min and then stopped by addition of 4140 µl of 5% acetic acid in DMF. The title compound was purified by RP-HPLC as follows: The sample was applied to a column (10×250 mm) of Lich rosorb RP-18 (7 µm) Merck, Germany, Art. 9394. The column was equilibrated with a mixture of 90% buffer A (50 mM tris, 75 mM $(NH_4)_2SO_4$ adjusted to pH 7.0 with $H_2SO_4$, 20% $CH_3CN$) and 10% of buffer B (80% $CH_3CN$). The sample was applied to the column and eluted with a linear gradient from 10% to 90% of buffer B in buffer A at a flow rate of 4 ml/hour at 40° C. The fractions containing the title compound were evaporated to dryness, dissolved in 50% acetic acid and desalted by gel filtration at 4° C. employing of column (16×150 mm) of BIO GEL P2 (BIO RAD, California, USA). The fractions containing the desired product were diluted with water and freeze dried. The yield was 2 mg. The identity of the compound was confirmed by PDMS.

Molecular mass, found by PDMS: 2033, theory 2032.

Determination of protraction in pigs

The title peptide derivative of Example 4 was $^{125}$I-labelled with Boulton & Hunters reagent (Bolton et al., Biochem. J., Vol. 133, pp. 529–39 (1973)) as follows: 50 nmol of peptide was dissolved in 1 ml of DMSO and subsequently 400 µl of DMF and 2 µl of N-ethylisopropylamine were added. The solution was added to an amount of Boulton et al. reagent containing 500 µCi of radioactivity. The reaction was allowed to proceed for 20 min. and then 10 µl of ethanola mi ine in DMF was added. The polypeptide was purified and isolated by RP-HPLC employing a column (4×250 mm) at a flow rate of 1 ml/min as described above.

As a measure of the protraction, the disappearance rate in pigs was studied and $T_{50\%}$ was determined. $T_{50\%}$ is the time when 50% of the $^{125}$I-labelled peptide has disappeared from the site of injection as measured with an external γ-counter (Ribel, U et al., The Pig as a Model for Subcutaneous Absorption in Man. In: Serrano-Rios et al., (Eds): Diabetes 1985; Proceedings of the 12th Congress of the International Diabetes Federation, Madrid, Spain, 1985 (Excerpta Medica, Amsterdam, pp. 891–96 (1986)).

Subcutaneous injection of the $^{125}$I-labelled peptide derivative in pigs showed a $T_{50\%}$ of 1.7±0.5 h (n=4), whereas the non tetradecanoylated, $^{125}$I-labelled reference peptide showed a $T_{50\%}$ of 0.7±0.1 h.

Reference

The $^{125}$I-labelled reference peptide was synthesized from Fmoc-Arg$^4$,Arg$^9$,Lys$^{15}$ somatostatin. Thus, 20 mg of Fmoc-Arg$^4$,Arg$^9$,Lys$^{15}$ somatostatin was dissolved in 1000 µl of 20% piperidine/DMF. After 20 min the product was purified by RP-HPLC, desalted and freeze dried and labelled with Boulton & Hunters reagent as described in Example 4.

Example 5
Synthesis of $Lys^{15}(N^\epsilon$-tetradecanoyl) atrial natriuretic peptide.

Human (H-Ser-Leu-Arg-Arg-Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr-Lys ($N^\epsilon$-tetradecanoyl)-OH) (H-(SEQ ID NO:5)($N^\epsilon$-tetradecanoyl)-OH) was synthesized by standard Fmoc solid phase peptide synthesis (Methods in Molecular Biology, Vol 35: Peptide Synthesis Protocols). The $\epsilon$-amino group of the C-terminal lysine was acylated using tetradecanoic acid succinimidyl-N-hydroxy ester according to the procedure described below. The synthesis was performed manually in polypropylene syringes, on a resin based on a low cross linked polystyrene backbone grafted with polyoxyethylene (TentaGel Resin).

Procedure:

One gram of resin was added 3 equivalents of the acid labile linker 4-hydroxy methylphenoxyacetic acid (HMPA). 3 equivalents of Fmoc-Lys(Dde)-OH was coupled as the first amino acid, with 0.5 equivalent of 4-dimethylaminopyridine as activating reagent. The Fmoc-protecting group was cleaved with 20% piperidine/DMF for 30 minutes. All other amino acids were coupled as $N^\alpha$-Fmoc protected amino acids with a mixture of DIC/HOBT (1:1 eq) in DMF as activating reagents. The amino acid Cys, was coupled as Fmoc-Cys(Acm)-OH. The cysteines were deprotected and oxidized by treatment with 10 mM Iodine in DMF for 2 minutes. After the last Fmoc-protecting group was removed, the $N^\alpha$-group of the last coupled amino acid was protected with the Boc group by coupling with 5 equivalents of di-tert-butyl-dicarbonate. The Dde-protecting group of $N^\epsilon$-Lys was cleaved with 2% hydrazine/DMF for 20 minutes, and the free $N^\epsilon$-group was acylated with 5 equivalents of tetradecanoic acid succinimidyl-N-hydroxy ester.

The Boc-, tBu-protecting groups and the HMPA-linker were cleaved with 95% TFA/5% $H_2O$ for 1.5 hour. The TFA/$H_2O$ was evaporated under reduced pressure, and the peptide was precipitated in diethyl ether as the HCl-salt, and freeze dried from a 10 mM ammonium hydrogen carbonate (pH 8.8). The overall yield was 35 mg. By N-terminal sequencing the product was shown to have the correct sequence.

Molecular mass, found by PDMS: 3417, which corresponds to the calculated mass plus sodium.

Example 6
$Lys^{30}(N\epsilon$-decanoyl) glucagon.

The title compound was purchased from Saxon Biochemicals GMBH, Hannover, Germany, as custom synthesis.

4.32 mg $Lys^{30}(N^\epsilon$-decanoyl), glucagon (equivalent to 4 mg glucagon) was dissolved in 4 ml of 1.8 mM hydrochloric acid added 0.9% sodium chloride and pH of the solution was measured to 2.7. The resulting solution was sterilized by filtration and transferred to a vial.

Two groups of rabbits (n=6 in each) were injected with 2 IU/animal of Insulin Actrapid at time −60 min. At time t=0 group 1 was injected SC with molar equivalent of 0.54 mg of $Lys^{30}(N^\epsilon$-decanoyl) glucagon/rabbit and group 2 injected SC with 0.5 mg of glucagon/rabbit. Blood was sampled at times: −60, 0, 15, 30, 60, 120, 180 and 240 min, and the glucose concentration determined by the hexokinase method. The resulting blood glucose concentrations are given in the table in mg glucose/100 ml:

| min | −60 | 0 | 15 | 30 | 60 | 120 | 180 | 240 |
|---|---|---|---|---|---|---|---|---|
| glucagon | 98 | 49 | 93 | 102 | 111 | 94 | 88 | 67 |
| glucagon derivative | 94 | 51 | 79 | 93 | 114 | 112 | 116 | 110 |

As it appears from the table, the blood glucose raising effect of glucagon is retained in $Lys^{30}(N^\epsilon$-decanoyl) glucagon but with a prolonged action.

---

---

We claim:

1. A peptide derivative which is:

Lys$^{30}$(N$^\epsilon$-lipophilic substituent) glucagon, wherein the lipophilic substituent has 8 to 40 carbon atoms and (a) is a straight chain fatty acid or (b) consists of a spacer selected from the group consisting of Glu and Asp, wherein said spacer forms one amide bond with the $\epsilon$-amino group of Lys$^{30}$ and a further amide bond with the carboxyl group of a straight chain fatty acid.

2. The peptide derivative of claim 1, wherein the lipophilic substituent is tetradecanoyl.

3. The peptide derivative of claim 2, wherein the lipophilic substituent is decanoyl.

* * * * *